United States Patent [19]

Wallach

[11] Patent Number: 5,000,960
[45] Date of Patent: Mar. 19, 1991

[54] PROTEIN COUPLING TO LIPID VESICLES

[75] Inventor: Donald F. H. Wallach, Brookline, Mass.

[73] Assignee: Micro-Pak, Inc., Wilmington, Del.

[21] Appl. No.: 300,079

[22] Filed: Jan. 19, 1989

Related U.S. Application Data

[63] Continuation-in-part of Ser. No. 157,571, Mar. 8, 1988, Pat. No. 4,911,928, which is a continuation-in-part of Ser. No. 25,525, Mar. 13, 1987, abandoned, Ser. No. 78,658, Jul. 28, 1987, Pat. No. 4,855,090, and Ser. No. 124,824, Nov. 24, 1987, Pat. No. 4,917,951.

[51] Int. Cl.$^5$ .................. A61K 9/127; A61K 37/22; A61K 49/00
[52] U.S. Cl. .................. 424/450; 264/4.3; 424/1.1; 424/7.1; 424/85.8; 424/420; 428/402.2; 436/523; 436/526; 436/829; 514/963
[58] Field of Search .................. 264/4.3; 428/402.2; 424/85.8, 420, 450, 7.1; 436/829; 514/963

[56] References Cited

U.S. PATENT DOCUMENTS

| | | | |
|---|---|---|---|
| 3,372,201 | 3/1966 | Leary et al. | 260/615 |
| 3,957,971 | 5/1976 | Oleniacz | 424/70 |
| 4,133,874 | 1/1979 | Miller et al. | 424/450 |
| 4,182,330 | 1/1980 | Michaels | 128/260 |
| 4,217,344 | 8/1980 | Vanlerberghe et al. | 428/402.2 X |
| 4,235,871 | 11/1980 | Papahadjopoulos et al. | 424/450 |
| 4,241,046 | 12/1980 | Papahadjopoulos et al. | 424/450 |
| 4,247,411 | 1/1981 | Vanlerberghe et al. | 264/4.6 |
| 4,348,329 | 9/1982 | Chapman et al. | 260/403 |
| 4,356,167 | 10/1982 | Kelly et al. | 424/450 |
| 4,377,567 | 3/1983 | Geho | 424/1.1 |
| 4,429,008 | 1/1984 | Martin et al. | 428/402.2 |
| 4,485,054 | 11/1984 | Mezei et al. | 264/4.6 |
| 4,536,324 | 8/1985 | Fujiwara et al. | 252/311 |
| 4,544,545 | 10/1985 | Ryan et al. | 424/1.1 |
| 4,564,599 | 1/1986 | Janoff et al. | 436/507 |
| 4,603,044 | 7/1986 | Geho et al. | 424/9 |
| 4,605,630 | 8/1986 | Kung et al. | 428/402.2 X |
| 4,608,211 | 8/1986 | Handjani et al. | 264/4.6 |
| 4,610,868 | 9/1986 | Fountain et al. | 424/1.1 |
| 4,619,913 | 10/1986 | Luck et al. | 514/2 |
| 4,666,711 | 5/1987 | Vanlerberghe et al. | 424/70 |
| 4,684,625 | 8/1987 | Eppstein et al. | 514/19 |
| 4,692,433 | 9/1987 | Hostetler et al. | 514/12 |
| 4,695,554 | 9/1987 | O'Connell et al. | 436/528 |
| 4,725,442 | 2/1988 | Haynes | 424/490 |
| 4,731,210 | 3/1988 | Weder et al. | 264/4.3 |
| 4,744,989 | 5/1988 | Payne et al. | 424/490 |
| 4,772,471 | 9/1988 | Vanlerberghe et al. | 424/450 |
| 4,804,539 | 2/1989 | Guo et al. | 424/450 |
| 4,853,228 | 8/1989 | Wallach et al. | 424/450 |
| 4,855,090 | 8/1989 | Wallach | 264/4.3 X |

FOREIGN PATENT DOCUMENTS

| | | |
|---|---|---|
| 0032578 | 7/1981 | European Pat. Off. . |
| 0144084 | 6/1985 | European Pat. Off. ............ 436/829 |
| 0167825 | 1/1986 | European Pat. Off. . |
| 3410602 | 9/1984 | Fed. Rep. of Germany . |
| 9106423 | 9/1984 | Japan . |
| 1207324 | 9/1986 | Japan . |
| 85/01440 | 4/1985 | PCT Int'l Appl. . |
| 87/06499 | 5/1987 | PCT Int'l Appl. . |
| 1539625 | 1/1979 | United Kingdom . |
| 2078543 | 1/1982 | United Kingdom . |
| 2079179 | 1/1982 | United Kingdom . |
| 2147263 | 5/1985 | United Kingdom . |
| 2198947 | 6/1988 | United Kingdom . |

OTHER PUBLICATIONS

McCutcheon's 1973 North American Edition, "Detergents and Emulsifiers", p. 27.
McCutcheon's 1982 North American Edition, "Emulsifiers & Detergents", pp. 71 & 77.
Ostro, 1983, "Lipsomes", Marcel Dekker, Inc., pp. 246-249.
Handjani et al., "Less Niosomes" (1985), pp. 297-313.
Bangham et al., J. Mol. Biol. (1965), 13, pp. 238-252.
Gregoriadis, The New England Journal of Medicine (1976), v. 295, pp. 704-710.
Szoka et al., PNAS (1978), pp. 4194-4198.
Dousset et al., "Methodes de Preparation des Liposomes" (1980), pp. 41-72.
Philippot et al., Biochimica et Biophysia Acta (1983), v. 734, pp. 137-143.
Ribier et al., Colloids and Surface (1984), v. 10, pp. 155-161.
Puisieux et al., "Problemes Technologiques Poses Par l'Utilixation des Liposomes Comme Vecteurs de Substances Medicamenteuses" (1985), pp. 73-111.
Baillie et al., J. Pharm. Pharmacol. (1986), v. 38, pp. 502-505.
Baillie et al., J. Phar. Pharmacol. (1985), v. 37, pp. 863-868.
Philippot et al., Biochimica et Biophysia Acta (1985), v. 821, pp. 79-84.

*Primary Examiner*—Richard D. Lovering
*Attorney, Agent, or Firm*—Lahive & Cockfield

[57] ABSTRACT

A new method of coupling proteins and other targeting molecules to lipid vesicles has been developed. A bifunctional agent forms a covalent bond without damaging the lipid structure and permits retention of protein activity.

23 Claims, No Drawings

PROTEIN COUPLING TO LIPID VESICLES

REFERENCE TO RELATED APPLICATIONS

The present invention is a continuation-in-part of U.S. patent application Ser. No. 157,571, filed March 8, 1988 and now U.S. Pat. No. 4,911,928, which is a continuation-in-part of U.S. patent application Ser. No. 025,525, filed March 13, 1987, now abandoned; U.S. patent application Ser. No. 078,658, filed July 28, 1987, now U.S. Pat. No. 4,855,090, and U.S. patent application Ser. No. 124,824, filed Nov. 24, 1987, now U.S. Pat. No. 4,917,951.

BACKGROUND OF THE INVENTION

The present invention relates to the coupling of targeting molecules to lipid vesicles. More particularly, methods of coupling targeting molecules, e.g., proteins, to the lipid bilayers of lipid vesicles or liposomes are disclosed which allow a substantial number of targeting molecules to be coupled to each vesicle without decreasing the stability of the vesicle bilayers. Products made using these methods, including targeted vesicles, are also disclosed.

Almost since their discovery, the possible use of lipid vesicles, primarily the phospholipid lipid vesicles commonly known as liposomes, as agents for carrying materials to specific cell groups or organs in the body has been discussed. In order to accomplish this, targeting molecules must be attached to the surface of the vesicle. These targeting molecules, when reacted with, or embedded in, the outer surface of the lipid vesicles, cause a reaction between the targeting molecules and a desired feature of the targeted cell group, e.g., a cell surface receptor or an antigenic feature on a cell. Currently used methods of coupling phospholipid vesicles to proteins rely primarily on reacting a bifunctional reagent with the amino group of phosphatidylethanolamine included in the bilayer and coupling the protein to the other end of the bifunctional molecule in the lipid layer. However, this procedure leads to many problems including breakdown of the lipid layer and resulting instability of the lipid vesicles. Another approach has been to couple targeting proteins to palmitic acid chains in the bilayer. However, only a few targeting molecules can be introduced in this way and the same complications arise. Accordingly, only small quantities of targeted molecules have been able to be attached to the vesicle without vesicle breakdown.

Similar coupling procedures can be used for in vitro diagnostic agents, particularly immunodiagnostics, as are used for targeting vesicles. As expected, the same type of problems have been observed concerning vesicle stability.

Accordingly, an object of the invention is to provide a method of coupling proteins or other targeting molecules to lipid vesicles which providing high levels of coupling while reducing vesicle breakdown.

A further object of the invention is to provide a method of coupling targeting molecules to lipid vesicles which can be used with both phospholipid and non-phospholipid vesicles.

Another object of the invention is to provide a method of coupling proteins to lipid vesicles which does not cause a loss of activity of the protein function.

These and other objects and features of the invention will be apparent from the following description and the claims.

SUMMARY OF THE INVENTION

The present invention features a method of coupling proteins and other targeting molecules to lipid vesicles at high frequency while retaining their chemical activity. The method can be used with any lipid vesicle which contains a steroid such as cholesterol as one of its structural components.

Lipid vesicles useful in the methods of the invention have steroids with a free sulfhydryl or SH group incorporated as one of the structural molecules of the lipid phase. This yields a vesicle with free SH groups. The preferred steroid is thiocholesterol which is functionally very similar to cholesterol and can be introduced into the bilayer at more than 20% molar ratio.

The protein or other targeting molecule to be coupled to the vesicle is modified by reaction with a bifunctional agent which reacts with a free $NH_2$ group on the targeting molecule and provides a free sulfhydryl group available for attachment to the vesicle. The modified targeting molecule, which retains its chemical activity after the modification, is then reacted with the lipid vesicle containing the free sulfhydryl group under conditions such that a S—S bond is formed, thereby covalently linking the targeting molecule to the vesicle. Preferred bifunctional agents are selected from a group consisting of N-hydroxysuccinimidyl 3-(2-pyridyldithio) propionate, derivatives and chemical analogs thereof.

Proteins are the targeting molecule of choice for use in the invention. Preferred proteins are lectins, particularly those selected from a group consisting of concanavalin A, wheat germ agglutinin, derivatives, and chemical analogs thereof, and immunoglobulins, particularly monoclonal antibodies and other IgG's and IgM's. Multiple copies of the bifunctional agent can be used on a single protein; in fact, modification of one to ten amino groups per protein is preferred. This is easily accomplished with the bifunctional groups disclosed herein. Other targeting molecules useful in the invention include the peptide hormones.

Although any lipid vesicles could be used in the method of the invention, nonphospholipid vesicles, particularly nonphospholipid paucilamellar lipid vesicles, are preferred. These vesicles may be made from a broad spectrum of materials including polyoxyethylene fatty esters, polyoxyethylene fatty acid ethers, diethanolamines, long-chain acyl amino acid amides, long-chain acyl amides, polyoxyethylene sorbitan mono and tristearates and oleates, polyoxyethylene glyceryl monostearates and monooleates, and glyceryl monostearates and monooleates. In addition to the lipid, steroids such as cholesterol and thiocholesterol are included as structural units and charge-producing materials may also be added.

The invention further features a number of uses of the targeting molecule-vesicle combination. One such use is a method of delivering an encapsulated material to a particular location in a human or animal by encapsulating the material within the lipid vesicle, modifying a proteinaceous targeting molecule such as a immunoglobulin, e.g., a monoclonal or chimeric antibody, or a portion or fragment thereof, with a bifunctional agent that react with free $NH_2$ groups on the protein and reacts with free sulfhydryl groups on the lipid vesicle, reacting the modified targeting molecule and the lipid vesicle so that one or more targeting molecules are on the surface of the lipid vesicle, introducing the targeted lipid vesicle into the animal or human subject, and allowing the targeting molecule to react with the specified target, thereby bringing the encapsulated material to the specified location. Preferred lipid vesicles for this use are nonphospholipid paucilamellar lipid vesicles as previously described because of their large carrying capacity for encapsulated material.

Another advantageous use is for in vitro and in vivo diagnostics and test materials particularly as immunodiagnostic agents. Visualization agents, magnetic particles, high density particles, or other materials which permit vesicle separation are encapsulated and a receptor or other reactive protein such as an immunoglobulin is bound to the surface of the lipid vesicle. The vesicles are then used in standard immunological or other receptor ligand reactions as visualization or separation agents.

The invention and its features will be further explained by the following detailed description.

DETAILED DESCRIPTION OF PREFERRED EMBODIMENTS

The method of the invention can be used to couple substantially any targeting molecule with free $NH_2$ groups to a lipid vesicle in which thiocholesterol can replace steroids such as cholesterol as a structural component. Proteins are preferred since there are normally a number of free amino groups on the protein which are not involved in its biological activity. These free $NH_2$ groups can be used to react with the bifunctional agent while allowing the protein to retain its normal activity. The present procedure is particularly useful with lectins such as concanavalin A or wheat germ agglutinin, or immunoglobulins such as IgG. If the immunoglobulins such as monoclonal or chimeric antibodies, or portions or fragments thereof, are used, these make particularly good targeting molecules allowing delivery of the lipid vesicle, including any encapsulated material, to a specified cell type or as an immunodiagnostic tool. Other targeting molecules having free $NH_2$ groups can also be used.

Although any type of lipid vesicle may be used, nonphospholipid paucilamellar lipid vesicles are preferred. These type of vesicles, and their methods of manufacture, are described in detail in co-pending U.S. patent application Ser. No. 157,571, now U.S. Pat. No. 4,911,928. In addition, the materials and methods described in co-pending U.S. patent application Ser. No. 124,824, now U.S. Pat. No. 4,917,951, can be used. Nonphospholipid materials useful in the present invention include surfactants selected from a group consisting of polyoxyethylene fatty esters having the formula $$R_1\text{—COO}(C_2H_4O)_n H$$

where $R_1$ is lauric, myristic, cetyl, stearic, or oleic acid, or their derivatives and $n = 2-10$;

polyoxyethylene fatty acid ethers, having the formula $$R_2\text{—CO}(C_2H_4O)_m H$$

where $R_2$ is lauric, myristic, or cetyl acids or their derivatives, single or double unsaturated octadecyl acids or their derivative, or double unsaturated eicodienoic acids or their derivatives and m ranges from 2-4;

diethanolamines, having the formula $$(HOCH_2\text{—}CH_2)_2 NCO\text{—}R_3$$

where $R_3$ is caprylic, lauric, myristic or linoleic acids or their derivatives;

long chain acyl hexosamides having the formula $$R_4\text{—NOCO—}(CH_2)_b\text{—}CH_3$$

where b ranges from 10-18 and $R_4$ is a sugar molecule selected from a group consisting of glucosamine, galactosamine, and N-methylglucamine;

long chain acyl amino acid amides having the formula $$R_5\text{—CHCOOH—NOC—}(CH_2)_c\text{—}CH_3$$

where c ranges from 10-18 and $R_5$ is an amino acid side chain;

long chain acyl amides having the formula $$HOOC\text{—}(CH_2)_d\text{—}N(CH_3)_2\text{—}(CH_2)_3\text{—}NCO\text{—}R_6$$

where $R_6$ is an acyl chain having 12-20 carbons and not more than two unsaturations, and d ranges from 1-3:

polyoxyethylene (20) sorbitan mono- or trioleate;

polyoxyethylene glyceryl monostearate or monooleate with 1-10 polyoxyethylene groups;

and glycerol monostearate or monooleate.

The surfactants can also be selected from a group consisting of polyoxyethylene (n) cetyl ethers or polyoxyethylene (n') cetyl amines, where n and n' each range from 5-10, polyoxyethylene (x, y, or z) stearyl, oleyl or linoleyl ethers, each having 2-10 polyoxyethylene units per acyl chain (x, y, and z range from 2-10), polyoxyethylene (x', Y', or z') stearyl, oleyl, or linoleyl amines having 5-10 polyoxyethylene units per acyl chain (x', y', and z' range from 5-10, of polyoxyethylene (s) eicosamonoenoyl or polyoxyethylene (t) eicosadienoyl ethers where s and t ranges from 2-10, the corresponding amines, polyoxyethylene (s') eicosamonoenoyl and polyoxyethylene (t') eicosadienoyl amines, having 5-10 polyoxyethylene units per acyl group (s' and t' range from 5-10), and other 20 carbon acyl polyoxyethylene derivatives, either ethers or amines, having differing amounts of unsaturation depending on the specific location of the double bonds.

The lipophilic phase consisting of the structural lipids, structural steroids, and any other lipophilic materials is blended with an aqueous phase consisting of an aqueous buffer and any aqueous soluble materials to be encapsulated, under shear mixing conditions, to form the paucilamellar lipid vesicles. "Shear mixing" is defined as the mixing of the lipophilic phase with the aqueous phase under turbulent or shear conditions which provide adequate mixing to hydrate the lipid and form lipid vesicles. The pump speeds are modified depending on the viscosity of the materials and the size of the orifices selected. "Shear mixing" is achieved by liquid shear which is substantially equivalent to a relative flow rate for the combined phases of about 5-30 m/s through a 1 mm radius orifice.

The invention also can be used for paucilamellar lipid vesicles having oil-soluble or oil-suspendable materials encapsulated therein. These vesicles are made by a procedure commencing with dispersing the material to be encapsulated in an oil or wax forming an oily phase. The oil or wax is a water immiscible oily solution selected from a group consisting of oils, waxes, natural and synthetic triglycerides, acyl esters, and petroleum derivatives, and their analogues and derivatives. The terms "disperse" or "dispersion" as used herein include dissolving or forming a suspension or colloid to yield a flowable phase. The oily phase containing the oil-dispersible material is mixed with the lipid phase and the combined oil-lipid phase is blended under shear mixing conditions with the aqueous phase. Surfactants useful in the encapsulation process are the same as those used to make paucilamellar lipid vesicles with an aqueous core. These vesicles can then be used in the coupling process described herein.

In preferred embodiments of the invention, charge producing materials and steroids such as thiocholesterol are used in the formation of the paucilamellar lipid vesicles. Preferred negative charge producing materials are dicetyl phosphate, cetyl sulphate, phosphatidic acid, phosphatidyl serine, oleic acid, palmitic acid, or mixtures thereof. In order to provide a net positive charge to the vesicles, long chain amines, e.g., stearyl amines or oleyl amines, long chain pyridinium compounds, e.g., cetyl pyridinium chloride, quaternary ammonium compounds, or mixtures of these can be used. In addition, classic phospholipid materials may also be used for multilamellar lipid vesicles.

As noted, in addition to other uses, vesicles made using the methods disclosed herein can be used in diagnostic testing, e.g., agglutination testing for immunological systems. The vesicles can also be used as markers or labels for visualization, e.g., swelling or shrinking in the presence of an immune reaction, or for radiography or NMR.

Hydrophilic materials which can be encapsulated in the vesicles include macromolecules, viruses, immunological adjuvants such as muramyl dipeptide, peptide hormones such as insulin, calcitonin and glucagon, hypothalmic peptides, pituitary hormones, growth factors such as angiogenic, epithelial and epidermal growth factors, lymphokines such as interleukin-2 and interferon, blood proteins such as hemoglobin and Factor VIII, water-soluble plant hormones and pesticides, radionucleotides, contrast materials for radiological and NMR diagnosis, cancer cytostatics, and antibiotics. Examples of lipophilic materials which can be encapsulated include steroid hormones, pheromones, porphyrins, organic pesticides, fungicides, insect repellants, and lipophilic vitamins and derivatives. Oil based materials include some additional lipophilic materials and materials which form colloids or suspensions in oil. A more complete listing of the types of pharmaceuticals that could be encapsulated in lipid vesicles is included in Gregoriadis, G. ed. *Liposome Technology* (CRC, Boca Raton, Fl.), Vols. 1-3 (1984).

The paucilamellar lipid vesicles can be made by a variety of devices which provides sufficient shear for shear mixing. There are a large variety of these devices available on the market including a microfluidizer such as is made by Biotechnology Development Corporation, a "French"-type press, or some other device which provides a high enough shear force and the ability to handle heated, semiviscous lipids. If a very high shear device is used, it may be possible to microemulsify powdered lipids, under pressure, at a temperature below their normal melting points and still form the lipid vesicles of the present invention.

A device which is particularly useful for making the lipid vesicles of the present invention has been developed by Micro Vesicular Systems, Inc., Vineland, N.J. and is further described in U.S. patent application Ser. No. 163,806, filed March 3, 1988, and now U.S. Pat. No. 4,895,542. Briefly, this device has a substantially cylindrical mixing chamber with at least one tangentially located inlet orifice. One or more orifices lead to a reservoir for the lipophilic phase, mixed with an oil phase if lipid-core PLV's are to be formed, and at least one of the other orifices is attached to a reservoir for the aqueous phase. The different phases are driven into the cylindrical chamber through pumps, e.g., positive displacement pumps, and intersect in such a manner as to form a turbulent flow within the chamber. The paucilamellar lipid vesicles form rapidly, e.g., less than 1 second, and are removed from the chamber through an axially located discharge orifice. In a preferred embodiment, there are four tangentially located inlet orifices and the lipid and aqueous phases are drawn from reservoirs, through positive displacement pumps, to alternating orifices. The fluid stream through the tangential orifices is guided in a spiral flow path from each inlet or injection orifice to the discharge orifice. The flow paths are controlled by the orientation or placement of the inlet or injection orifices so as to create a mixing zone by the intersection of the streams of liquid. The pump speeds, as well as the orifice and feed line diameters, are selected to achieve proper shear mixing for lipid vesicle formation. As noted, in most circumstances, turbulent flow is selected to provide adequate mixing.

No matter what device is used to form the paucilamellar lipid vesicles, if proper shear mixing is achieved they have a large, unstructured amorphous center surrounded by a plurality of lipid bilayers having aqueous layers interspersed therebetween. About four lipid bilayers is standard with 2-10 possible. The amorphous center may be entirely filled with an aqueous material, e.g., a buffer and any aqueous material to be encapsulated, or may be partially or totally filled with an oily material, forming lipid-core PLV's. If an aqueous center is used, the paucilamellar lipid vesicles will normally range in diameter from about 0.5-2 $\mu$ while if an oily center is used, the size may increase to up to about 15-20 $\mu$ depending upon the amount of oil used.

The following nonlimiting examples will further explain and illustrate the methods and procedures of the invention.

EXAMPLE 1

Lectin Modification

A. General Reactions

In this Example, two lectins, concanavalin A ("Con A") and wheat germ agglutinin ("WGA"), were modified using a preferred bifunctional coupling agent, N-hydroxysuccinimidyl 3-(2-pyridyldithio) propionate ("SPDP"). The basic reactions involved are as follows:

Protein-NH$_2$ +     I

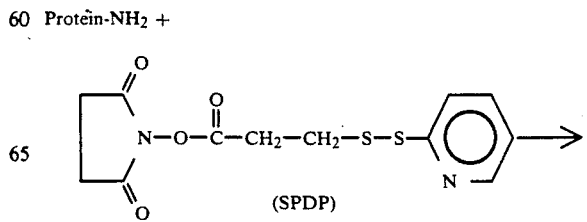

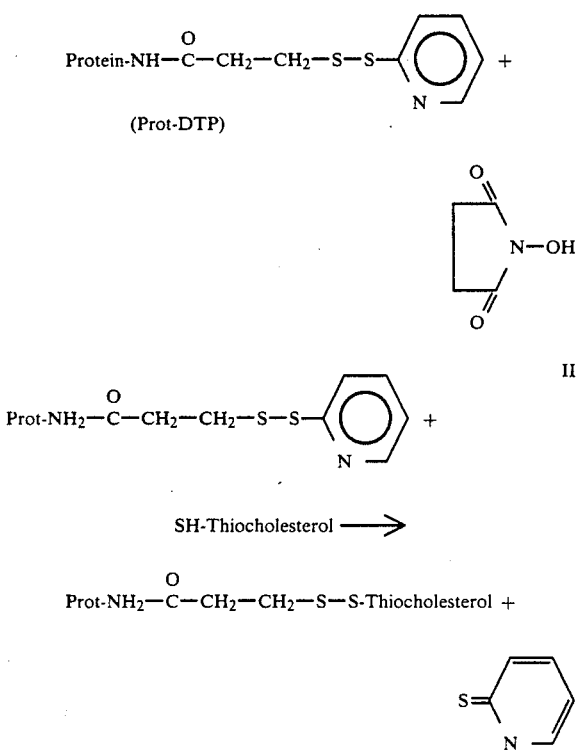

Once the SPDP is bound to the protein, forming a protein-dithiopropionate compound ("Prot-DTP"), the Prot-DTP can be coupled to the lipid vesicles containing a sulfhydryl group. The preferred lipid vesicles are paucilamellar lipid vesicles having a portion of the cholesterol used in forming the lipid vesicle replaced by thiocholesterol, yielding free SH groups. These free SH groups are coupled to the Prot-DTP by a covalent S—S bond. The number of protein molecules bound per lipid vesicle can be modified by changing the number SPDP molecules bound to each molecule of protein, changing the amount of substitute protein (Prot-DTP) in contact with the lipid vesicles, and changing the percentage of the thiocholesterol in the lipid vesicles.

B. Concanavalin A-SPDP Bonding

In the first experiment, 0.01 mMoles of Con A was incubated with varying amounts of SPDP for thirty minutes at room temperature. Stock solutions, specifically twenty-five mM solutions of the Con A in phosphate buffered saline, pH 7.5, 40 mM SPDP in methanol, and 50 mM dithiothreitol ("DTT") in distilled water, were used. Unreacted SPDP was eliminated by gel filtration through a PD10 gel column equilibrated with phosphate buffered saline, pH 7.5. Fractions were collected and the Con A-DTP complex was found to be concentrated in the void volume.

The DTP to protein binding ratio was determined using the following procedure. Approximately 0.5 ml of phosphate buffered saline was added to each fraction (bringing each fraction to approximately 1.0 ml) and 100 μl of DTT was added. The absorbance of the resulting pyridin-2-thione was measured at 343 nm. Table 1 shows the results of these experiments.

TABLE 1

| Con A (moles) | SPDP (Vol ml) | SPDP (umoles) | Ratio SPDP/Con A | DTP bound/Con A |
|---|---|---|---|---|
| 0.01 | 1.25 | 0.05 | 5 | 1.68 |
| 0.01 | 2.5 | 0.10 | 10 | 2.70 |
| 0.01 | 5.0 | 0.20 | 20 | 2.76, 4.2, 4.0 |
| 0.01 | 10.0 | 0.40 | 40 | 4.6 |
| 0.01 | 20.0 | 0.80 | 80 | 1.6 |

As can be seen from Table 1, changing the amounts of SPDP modifies the amount of DTP bound per mole of lectin. Values of excess of four are relatively easy to obtain.

C. WGA-SPDP Binding

In this experiment, the same procedure was used to couple the WGA to SPDP as was used to couple the Con A in paragraph B, except a SPDP/WGA ratio of twenty was used. The same stock solutions were used except a 25 mM solution of WGA was substituted for the Con A. Upon assay with DTT using the procedure previously described, approximately twelve SPDP molecules were bound to each WGA molecule.

D. Forming a Fluorescent WGA Conjugate

In this experiment, the WGA was replaced with a WGA-fluoroscein isothiocyanate conjugate (WGA-FITC) purchased from Sigma Chemical Company. The same procedures were used to couple the SPDP bifunctional agent to the WGA-FITC as have been described for coupling the WGA itself. Upon DTT analysis, approximately ten DTP molecules were bound to each WGA-FITC molecule. The WGA-FITC has substantially the same reactivity as WGA.

EXAMPLE 2

Coupling of Protein to Lipid Vesicles

A. Formation of Lipid Vesicles

In this Example, paucilamellar lipid vesicles were made using a syringe method to hydrate the lipid. The lipophilic phase is placed in one syringe, the aqueous phase (buffer) in another syringe coupled to the first by a stopcock, and the material is blended and formed into vesicles by transfer from syringe to syringe.

Table 2 lists the materials used to form "control" and "sample" lipid vesicles. The control vesicles are substantially identical to the sample vesicles except that almost two-thirds of the cholesterol is replaced with thiocholesterol in the sample vesicles. The materials used other than cholesterol are Brij 52 (ICI Americas) (polyoxyethylene (2) cetyl ether) as the main structural component, and dicetyl phosphate ("DCP") as a charge-producing agent. The Brij 52 is blended with the cholesterol and/or thiocholesterol and the DCP at 50°–60° C. and hydrated with approximately 1.9 ml of phosphate buffered saline for about two minutes.

TABLE 2

| Material | "Control" mg | mmoles | % | "Sample" mg | mmoles | % |
|---|---|---|---|---|---|---|
| Brij 52 | 63 | 0.19 | 76 | 63 | 0.19 | 76 |
| Cholesterol | 22 | 0.058 | 23 | 8 | 0.02 | 8 |
| Thiocholesterol |  |  |  | 15 | 0.038 | 15 |
| DCP | 0.7 | 0.003 | 1 | 0.7 | 0.002 | 1 |

Paucilamellar lipid vesicles with a diameter of approximately 584 nm were formed in both the control and sample reactions. The sample vesicles had free SH groups for protein coupling.

B. Coupling of Thiocholesterol Lipid Vesicles and WGA-FITC-DTP

The following procedure was used to couple the WGA-FITC-DTP to the thiocholesterol-containing lipid vesicles. The WGA-FITC-DTP was formed using the procedure previously described by reacting 27 mg of WGA-FITC with 40 μmoles of SPDP. Recovery of the WGA-FITC-DTP was 1.6 ml at a concentration of approximately 1.35 mg/ml.

Three different amounts of WGA-FITC-DTP were mixed with 200 μl of the thiocholesterol modified lipid vesicles (2.5 micromoles lipids) and kept overnight at room temperature. Unreacted WGA-FITC-DTP was removed by centrifugation on a discontinuous dextran gradient. The gradient was prepared by mixing about 0.5 ml of the sample with 2 ml of 20% dextran and overlaying the sample successively with 2 ml of 15%, 10%, and 5% dextran. The dextran gradient containing the lipids was centrifuged for approximately 15 minutes at 3,500 rpm in a Beckman Table Top centrifuge. Unreacted lectins stay in the 20% layer while the lipid vesicles go to the top.

The fluorescence of the control and sample lipid vesicles were measured using an absorbance of 490 nm and an emission of 520 nm. The results, as compared with a WGA-FITC-DTP standard, are shown in Table 3. In all cases, a substantial binding to the lipid vesicles was observed. Three different amounts of WGA-FITC-DTP were used.

TABLE 3

|  | Assay (A) | (B) | (C) |
|---|---|---|---|
| WGA-FITC (1.35 mg/ml) | 0.121 mg (90 μl) | 0.430 mg (320 μl) | 0.810 mg (600 μl) |
| Lipids (200 μl) | 2.5 μmol | 2.5 μmol | 2.5 μmol |
| WGA-FITC Bound | 1.46 μmol | 4.8 μmol | 7.92 μmol |
| WGA-FITC Bound/Lipo | 7,800 | 26,000 | 42,000 |
| WGA-FITC Bound/SH-Chol | 1/63 | 1/19 | 1/12 |

These nonlimiting Examples show the efficacy of the present invention. These Examples, and the description herein, may lead others to further obvious modifications of the present invention. Such other modifications are included within the following claims.

What is claimed is:

1. A method of coupling targeting molecules to nonphospholipid lipid vesicles while retaining the targeting specificity of said targeting molecules comprising the steps of:
   selecting a targeting molecule having a free $NH_2$ group thereon,
   reacting said targeting molecule with a bifunctional agent comprising N-hydroxysuccinimidyl 3-(2-pyridyldithio)propionate, in a manner such that said bifunctional agent reacts with said $NH_2$ group on said targeting molecule to incorporate a free SH group onto said targeting molecule,
   forming a nonphospholipid lipid vesicle having a steroid with a free SH group as one of its structural components, and
   reacting said lipid vesicle having a free SH group thereon and said targeting molecule with said free SH group, thereby coupling said targeting molecule to said lipid vesicle.

2. The method of claim 1 wherein said steroid with a free SH group comprises thiocholesterol.

3. The method of claim 1 wherein said nonphospholipid lipid vesicle comprises polyoxyethylene fatty esters, polyoxyethylene fatty acid ethers, diethanolamines, long-chain acyl amino acid amides, long-chain acyl amides, polyoxyethylene sorbitan mono and tristearates and oleates, polyoxyethylene glyceryl monostearates and monooleates, and glyceryl monostearates and monooleates.

4. The method of claim 3 wherein said nonphospholipid lipid vesicle comprises a paucilamellar lipid vesicle.

5. The method of claim 4 wherein said nonphospholipid lipid vesicle further comprises a charge-producing agent as a structural component.

6. The method of claim 1 wherein said targeting molecule is selected from a group consisting of peptide hormones.

7. The method of claim 1 wherein said targeting molecule comprises a protein.

8. The method of claim 7 wherein said protein is selected from a group consisting of lectins, and immunoglobulins.

9. The method of claim 8 wherein said lectin is selected from a group consisting of concanavalin A, and wheat germ agglutinin.

10. The method of claim 8 wherein said immunoglobulin is selected from a group consisting of monoclonal antibodies, chimeric antibodies, and portions and fragments thereof.

11. A method of delivering a specified material to a particular location or tissue in a human or animal body comprising the steps of:
    encapsulating said specified material in a nonphospholipid lipid vesicle, said lipid vesicle containing a steroid having a free SH group as one of its structural components,
    selecting a proteinaceous targeting molecule which reacts with said particular location or tissue,
    reacting said proteinaceous targeting molecule with a bifunctional agent comprising N-hydroxysuccinimidyl 3-(2-pyridyldithio)propionate, in a manner such that said bifunctional agent reacts with free $NH_2$ groups on said targeting molecule and provides a free SH group, thereby forming a modified targeting molecule,
    reacting a plurality of said modified targeting molecules with said lipid vesicle so that at least one of said modified targeting molecules is bound to the surface of said lipid vesicle by an S—S bond,
    introducing said lipid vesicle having said modified targeting molecule bound thereto into said human or animal body, and
    allowing said targeting molecule to react with its target, thereby bringing said encapsulated material to said specified location or tissue.

12. The method of claim 11 wherein said nonphospholipid lipid vesicle comprises a paucilamellar lipid vesicle.

13. The method of claim 11 wherein said proteinaceous targeting molecule is selected from a group consisting of immunoglobulins.

14. The method of claim 13 wherein said immunoglobulin is selected from a group consisting of monoclonal antibodies, chimeric antibodies, and fragments and portions thereof.

15. A nonphospholipid lipid vesicle having a targeting molecule attached thereto comprising a nonphospholipid lipid vesicle containing a steroid having free SH groups as one of its structural components, said targeting molecule being attached to said lipid vesicle by an S—S bond between a free SH group on said targeting molecule and a free SH group on said lipid vesicle.

16. The lipid vesicle of claim 15 wherein said lipid vesicle comprises a paucilamellar lipid vesicle.

17. The lipid vesicle of claim 15 wherein said targeting molecule is selected from a group consisting of proteins, and peptide hormones.

18. The lipid vesicles of claim 17 targeting molecule is a protein selected from a group consisting of lectins, immunoglobulins, monoclonal antibodies, and chimeric antibodies.

19. The lipid vesicles of claim 15 wherein said targeting molecule is attached to said lipid vesicle by a bifunctional agent comprising N-hydroxysuccinimidyl 3-(2-pyridyldithio)propionate, in a manner such that said bifunctional agent attaches to a free $NH_2$ group on said targeting molecule and supplies a free SH group thereto.

20. The lipid vesicle of claim 15 wherein said vesicle has a diagnostic agent encapsulated therein.

21. The lipid vesicle of claim 20 wherein said targeting molecule comprises an immunoglobulin.

22. The lipid vesicle of claim 21 wherein said immunoglobulin is selected from a group consisting of monoclonal antibodies, chimeric antibodies, and portions and fragments thereof.

23. The lipid vesicle of claim 20 wherein said diagnostic agent is selected from a group consisting of immunodiagnostic agents, visualization agents, high density particles and magnetic particles.

* * * * *